US011662327B2

United States Patent
Hoeffner et al.

(10) Patent No.: US 11,662,327 B2
(45) Date of Patent: May 30, 2023

(54) SYSTEMS AND METHODS FOR CONTROLLING OXYGEN LEVELS

(71) Applicant: Sanofi, Paris (FR)

(72) Inventors: Kai Hoeffner, Cambridge, MA (US); Brooke Tam, Newton, MA (US); Jonathan Wang, Boston, MA (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 17/382,915

(22) Filed: Jul. 22, 2021

(65) Prior Publication Data

US 2022/0042942 A1 Feb. 10, 2022

Related U.S. Application Data

(60) Provisional application No. 63/062,134, filed on Aug. 6, 2020.

(30) Foreign Application Priority Data

Nov. 20, 2020 (EP) .................................... 20315463

(51) Int. Cl.
 *G01N 27/22* (2006.01)
 *G01R 27/26* (2006.01)

(52) U.S. Cl.
 CPC ......... *G01N 27/221* (2013.01); *G01N 27/226* (2013.01); *G01R 27/2605* (2013.01)

(58) Field of Classification Search
 CPC ............... G01N 27/221; G01N 27/226; G01R 27/2605; C12M 41/48; C12M 41/32
 See application file for complete search history.

(56) References Cited

U.S. PATENT DOCUMENTS

2015/0019140 A1* 1/2015 Downey .............. G01N 27/221 702/21
2019/0300841 A1* 10/2019 Aron ...................... C12M 41/12

FOREIGN PATENT DOCUMENTS

| CN | 110358683 A | * 10/2019 | ............ C12M 41/48 |
| CN | 110656044 | 1/2020 | |

(Continued)

OTHER PUBLICATIONS

International Search Report and Written Opinion in International Application No. PCT/US2021/042734, dated Nov. 5, 2021, 11 pages.

*Primary Examiner* — Alexander Satanovsky
*Assistant Examiner* — Asm Fakhruddin
(74) *Attorney, Agent, or Firm* — Fish & Richardson P.C.

(57) ABSTRACT

Sensors are configured to capture measurement data representing dissolved oxygen (DO) measurements of an environment and capacitance measurements of a medium of the environment. A memory includes computer-executable instructions. One or more processors are communicatively coupled to the one or more sensors and configured to execute the computer-executable instructions to carry out operations comprising: generating, using first measurement data captured by the one or more sensors, a model based on a relationship between the first set of DO measurements and the first set of capacitance measurements; receiving, from the one or more sensors, second measurement data; predicting, using the model and based on the new capacitance measurement, an expected DO measurement; determining whether to use the expected DO measurement or the new DO measurement; and controlling, a valve to cause the determined oxygen input amount to flow into the environment based on the expected DO measurement.

21 Claims, 3 Drawing Sheets

(56) References Cited

FOREIGN PATENT DOCUMENTS

| CN | 110656044 A | * | 1/2020 | |
|---|---|---|---|---|
| SE | 1300126 A1 | * | 8/2014 | ........... G05B 23/024 |
| WO | WO 2019/210405 | | 11/2019 | |
| WO | WO-2019210405 A1 | * | 11/2019 | ............ C12M 41/48 |

* cited by examiner

SYSTEMS AND METHODS FOR CONTROLLING OXYGEN LEVELS

CROSS-REFERENCE TO RELATED APPLICATIONS

This application claims priority to U.S. Provisional Application Ser. No. 63/062,134, filed Aug. 6, 2020 and European Application Serial No. EP 20315463.8, filed Nov. 20, 2020, the entire contents of which are herein incorporated by reference.

TECHNICAL FIELD

This disclosure generally relates to active environments, such as bioreactors.

BACKGROUND

A bioreactor can refer to any manufactured device or system that supports a biologically active environment. For example, a bioreactor can be a vessel in which a chemical process is carried out that involves organisms or biochemically active substances derived from such organisms. This process can either be aerobic or anaerobic. These bioreactors can be cylindrical, ranging in size from liters to cubic meters, and can be made of stainless steel. A bioreactor can also refer to a device or system designed to grow cells or tissues in the context of cell culture. Such devices can be developed for use in tissue engineering or biochemical/bioprocess engineering. A bioreactor may be classified as batch, fed batch or continuous (for example, a continuous stirred-tank reactor model). An example of a continuous bioreactor is a chemostat. Organisms growing in bioreactors can be submerged in a liquid medium or may be attached to the surface of a solid medium. Submerged cultures can be suspended or immobilized.

Dissolved oxygen (DO) can refer to the amount of oxygen that has been dissolved into a water source, such as in a bioreactor. Depending on the application, it may be essential to measure and keep track of the amount of dissolved oxygen in the water. When working with fermentation and cell culture, dissolved oxygen probes can be used for the measurement of dissolved oxygen within bioreactors and cell culture. Whether developing a new drug or studying the biochemistry of cells, the right amount of dissolved oxygen can be important for the bioreactor to work effectively. A low dissolved oxygen level in a bioreactor can cause problems with cell growth rate and the uptake of nutrients, which can have a negative effect on research and experiments. To avoid such issues, dissolved oxygen levels can be constantly measured using dissolved oxygen sensors.

DO concentration can be highly important for the growth and production of cell cultures. DO levels that are too high or too low can cause adverse effects. For example, when the DO levels become too low within bioreactors, growth rates can slow, nutrient uptake can worsen, and metabolite synthesis can be impacted, which can lead to a reduced quality for the end product and a lower yield. On the other hand, higher DO levels can lead to the development of reactive oxygen species, which may be highly unstable molecules that can cause cell death. Certain components of the substance can also become oxidized, which may cause cell mutations.

SUMMARY

In an aspect, a system is provided. The system includes one or more sensors configured to capture measurement data representing dissolved oxygen (DO) measurements of an environment and capacitance measurements of a medium of the environment. The system includes a computer-readable memory comprising computer-executable instructions. The system includes one or more processors communicatively coupled to the one or more sensors and configured to execute the computer-executable instructions, wherein when the one or more processors are executing the computer-executable instructions, the one or more processors are configured to carry out operations comprising: generating, using first measurement data captured by the one or more sensors during a first time interval and representing a first set of DO measurements and a first set of capacitance measurements, a model based on a relationship between the first set of DO measurements and the first set of capacitance measurements; receiving, from the one or more sensors, second measurement data captured by the one or more sensors during a second time interval and representing a new DO measurement and a new capacitance measurement; predicting, using the model and based on the new capacitance measurement, an expected DO measurement; determining whether to use the expected DO measurement or the new DO measurement for determining an oxygen input amount; and controlling, when it is determined to use the expected DO measurement, a valve to cause the determined oxygen input amount to flow into the environment based on the expected DO measurement. Other implementations can include methods, devices, computer-readable media, computer program products, and other technology.

Implementations can include some, all, or none of the following features. Determining whether to use the expected amount of dissolved oxygen or the new amount of DO comprises: determining a DO rate of change based on the new DO measurement and the first set of DO measurements; determining a capacitance rate of change based on the new capacitance measurement and the first set of capacitance measurements; and determining to use the expected DO measurement when the DO rate of change exceeds the capacitance rate of change by a rate of change threshold. A bioreactor, wherein the one or more sensors include a DO sensor and a capacitance sensor. Determining whether to use the expected DO measurement or the new DO measurement comprises: comparing the new capacitance measurement with a capacitance threshold; and determining to use the new DO measurement when the new capacitance measurement exceeds the capacitance threshold. Determining whether to use the expected DO measurement or the new DO measurement comprises: comparing the expected DO measurement and the new DO measurement; and determining to use the expected DO measurement when the expected DO measurement exceeds the new DO measurement. Receiving, from the one or more sensors, third measurement data captured by the one or more sensors during a third time interval and representing a second set of DO measurements and a second set of capacitance measurements; and updating the model based on the third measurement data. The third measurement data comprises the second measurement data.

Implementations of the present disclosure can provide one or more of the following advantages. When compared with traditional techniques, the amount of dissolved oxygen in an environment (for example, a bioreactor) can be regulated with increased precision and accuracy, cell culture and fermentation processes can be improved, and noise from sensor output can be reduced.

These and other aspects, features, and implementations can be expressed as methods, apparatus, systems, components, program products, means or steps for performing a function, and in other ways.

These and other aspects, features, and implementations will become apparent from the following descriptions, including the claims.

DETAILED DESCRIPTION

A bioreactor system (sometimes referred to in this specification as a bioreactor) can include a vessel having: an agitator for mixing the contents of the bioreactor system to keep the cells of the contents in a homogenous condition for better transport of nutrients and oxygen to a desired product; a baffle used to break vortex formations in the vessel; a sparger for supplying oxygen (dissolved oxygen) to the growing cells; and a jacket that provides an annular area for circulation of constant temperature of water. The bioreactor system can also include processing mechanisms, such as proportional-integral-derivative controllers (PID controllers) and mass flow controllers (MFCs) to control and maintain certain types of liquids or gasses entering the vessel. To facilitate the monitoring of dissolved oxygen (DO) in a bioreactor, DO sensors can be used to measure the amount of DO in a bioreactor. During cell growth, the amount of oxygen demand of the bioreactor can increase, resulting in an increase of continuous injection of oxygen bubbles to maintain the cell growth. However, these oxygen bubbles may interact with the DO sensor to cause the DO sensor to give a false reading (that is, they may cause the DO sensor to measure more DO in the bioreactor than DO actually in the bioreactor). The false readings can cause a reduction in accuracy of the processing mechanisms when they determine an amount of DO that should be added to the bioreactor for maintaining cell growth.

Systems and methods described in this specification can reduce the effects of the aforementioned disadvantages. In some implementations, a capacitance sensor is used along with the DO sensor to measure the capacitance (biomass) of the bioreactor over time. Cells with intact plasma membranes in a bioreactor (or fermenter) can be considered to act as capacitors under the influence of an electrical field. The non-conducting nature of the plasma membrane allows a build up of charge. The resulting capacitance can be measured, and can be proportional to the membrane bound volume of these cells. Thus, capacitance can be used as an orthogonal measurement of biomass (for example, cell density). In some implementations, the measured capacitance over time is used to generate a model (slope) of the relationship between the measured capacitances and the oxygen demand (O2 output from the MFC, actuator) to maintain the DO setpoint (targeted DO value) over time. It may be assumed that the oxygen demand for each cell will remain constant (that is, one can derive a oxygen uptake rate). Therefore, as capacitance increases, the increase in oxygen demand should increase at a constant rate (that is, in accordance with the oxygen uptake rate). Accordingly, in some implementations, the generated model can be used to predict an expected oxygen output in the bioreactor required to maintain the DO setpoint, and that expected amount of oxygen output can be used to determine an amount of oxygen gas to add to the bioreactor for nurturing cell growth and match the DO setpoint. In some implementations, the model is updated after a predetermined amount of time based on new measurement values. In some implementations, when a new DO measurement value is captured by the DO sensor, it is determined whether to use the new DO measurement value or the predicted DO measurement to determine how much oxygen is to be input into the bioreactor. In some implementations historical data of a comparison between oxygen output and capacitance can be utilized to determine how much oxygen is to be input into the bioreactor. This can be utilized in instances where DO measurement noise prevents the accurate generation of a relationship between oxygen output and capacitance. This determination can be based on a comparison of a determined rate of change of DO and a determined rate of change of capacitance, or it can be based on a comparison of the predicted amount of DO and the new DO value.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all implementations or that the features represented by such element may not be included in or combined with other elements in some implementations.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (for example, a bus), as may be needed, to affect the communication.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Several features are described hereafter that can each be used independently of one another or with any combination of other features. However, any individual feature may not address any of the problems discussed above or might only address one of the problems discussed above. Some of the problems discussed above might not be fully addressed by any of the features described herein. Although headings may be provided, data related to a particular heading, but not found in the section having that heading, may also be found elsewhere in this description.

Figure 1:
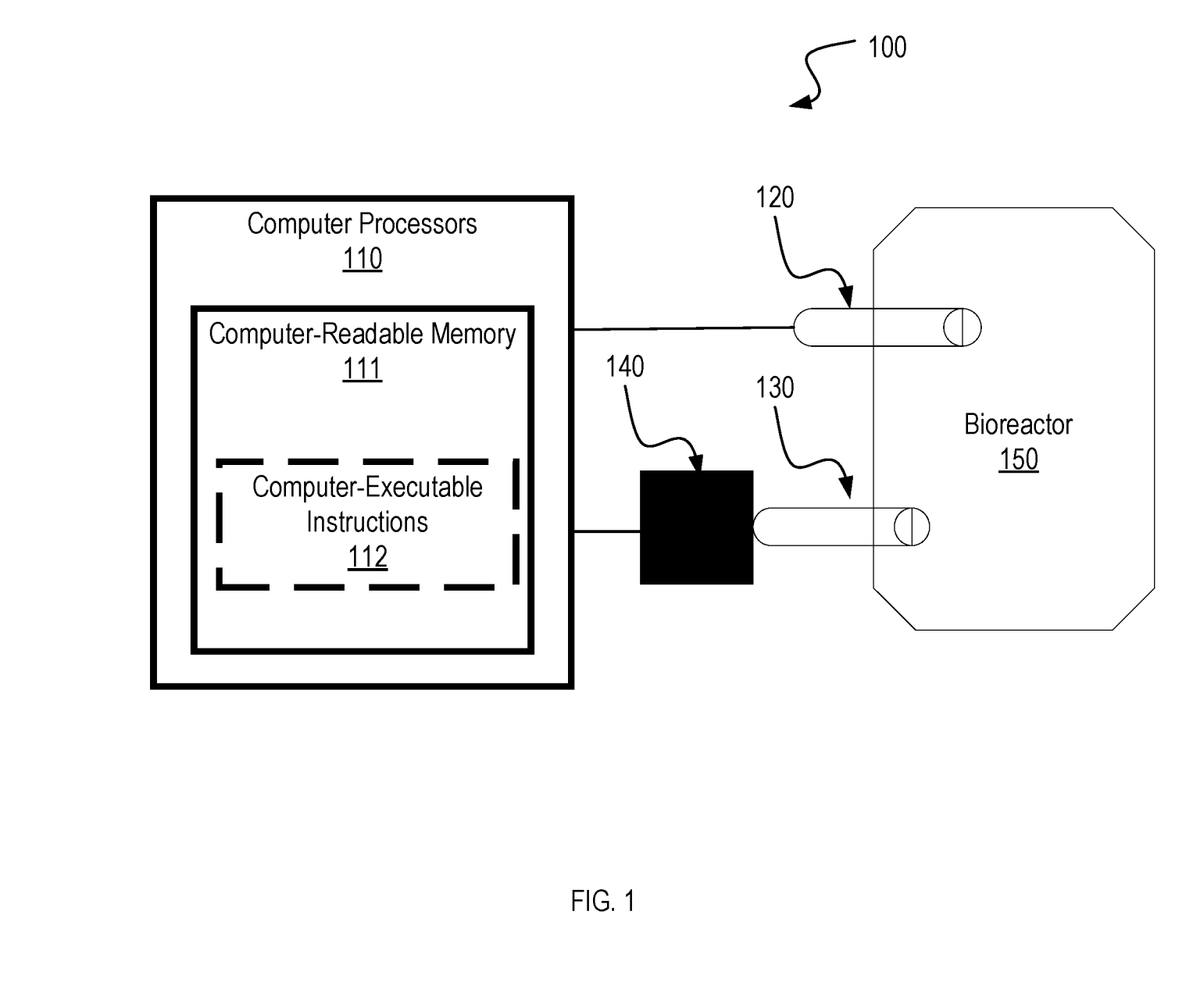
FIG. 1 is a block diagram illustrating an example system for controlling oxygen levels.

FIG. 1 is a block diagram illustrating an example system 100 for controlling oxygen levels. The system 100 includes one or more sensors 120, a sparger 130, a control valve 140, and computer processors 110.

The one or more sensors 120 include a DO sensor. In some implementations, the DO sensor includes an electrochemical DO sensor, such as a polarographic sensor or a galvanic sensor. In some implementations, the DO sensor includes an optical DO sensor. The DO sensor is configured to measure an amount of DO in a bioreactor 150, and generate measurement data representing the measured amount of DO. The one or more sensors 120 also include a capacitance sensor. The capacitance sensor is configured to measure an amount of capacitance of a medium (for example, a cell mass) in the bioreactor, and generate measurement data representing the measured amount of capacitance.

The control valve 140 is in fluid communication with an oxygen supply line and can be used to regulate the flow of oxygen into the bioreactor 150 through the sparger 130. As will be described later, the valve 140 can be controlled by the computer processors 110.

The computer processors 110 are communicatively coupled to the one or more sensors 120, and include computer-readable memory 111 and computer readable instructions 112. The computer-readable memory 111 (or computer-readable medium) can include any data storage technology type which is suitable to the local technical environment, including, but not limited to, semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the computer-readable memory 111 includes code-segment having executable instructions.

The computer processors 110 can include a general purpose processor, a central processing unit (CPU), and/or at least one application specific integrated circuit (ASIC). The computer processors 110 can also include general purpose programmable microprocessors, special-purpose programmable microprocessors, digital signal processors (DSPs), programmable logic arrays (PLAs), field programmable gate arrays (FPGA), special purpose electronic circuits, or a combination thereof. The computer processors 110 are configured to execute program code means such as the computer-executable instructions 112. In some implementations, the computer processors 110 include all or portions of a PID controller. In some implementations, the computer processors 110 include all or portions of a mass flow controller.

When executing the computer-executable instructions 112, the computer processors 110 are configured to receive the measurement data from the one or more sensors 120 and generate, based on the measurement data, a model based on a relationship between a plurality of oxygen output and a plurality of capacitance measurements. In some implementations, before generating the model, the computer processors are configured to apply an exponential (for example, a process variable (PV) filter) to the measurement data to reduce a predetermined amount of noise of the measurement data and correct the measured values of the measurement data based on the predetermined amount of noise. The predetermined amount of noise can be predetermined based on known design parameters and testing of the one or more sensors 120 and other system parameters (that is, it can be known how much noise the one or more sensors 120 will inherently add to the measurement data based on testing and calibration of the one or more sensors 120). In some implementations, the one or more sensors 120 are configured to capture measurement data at a measurement time interval. For example, the one or more sensors 120 can be configured to capture measurement data every 5 seconds, 10 seconds or 15 seconds. The computer processors 110 are then configured to plot a set of DO measurement values against a set of capacitance measurement values that were captured during a predetermined time interval (for example, an hour) to generate a slope. For example, if the one or more sensors 120 are configured to capture measurement data every 5 seconds, the computer processors 110 can plot, over the course of an hour, the DO measurement value measured at $t_0$ (time=0) against the capacitance measurement value measured at to, the DO measurement value measured at $t_1$ (time=5 seconds) against the capacitance measurement value measured at $t_1$, the DO measurement value measured at $t_2$ (time=10 seconds) against the capacitance measurement value measured at $t_2$, and so on. In some implementations, the model represents a slope and the computer processors 110 are configured to determine an average of the slope. In some implementations, the model can be updated with new measurement values after a predetermined amount of time (for example, every 720 seconds). For example, measurement values captured every 720 seconds after the hour interval can added to the model, and new slope averages can be determined (This is a moving average function, the new values kick out the old values in the array so the slope can change slowly, the 720 s can be modified).

Once the model is generated, the computer processors 110 receive new measurement data (including corresponding new measurement values for DO, capacitance, and the oxygen output) and are configured to use the model to determine an expected oxygen output amount based on the new capacitance measurement values. For example, for every new capacitance measurement value, the computer processors 110 can apply the model to determine an expected oxygen output value using the determined average slope. The computer processors 110 are then configured to determine whether to use the new oxygen output values or the expected oxygen output values to determine how much oxygen should be caused to flow into the bioreactor 150 through the sparger 130. In some implementations, this includes comparing a DO rate of change (RoC) with a capacitance RoC. For example, the RoC between the DO measurements can be compared with the RoC between the capacitance measurements. In some implementations, if the DO RoC is greater than the capacitance RoC, then the expected DO measurement is used for determining an amount of DO to add to the bioreactor. In some implementations, the capacitance RoC is a conversion of the real capacitance RoC to oxygen flow units. For example, the capacitance RoC can be the real change in capacitance over time multiplied by the oxygen output/capacitance slope determined previously to get an expected oxygen output RoC. In some implementations, if the expected oxygen output RoC is greater than the oxygen output RoC, the expected oxygen output measurement is used to determine an amount of oxygen to add to the bioreactor 150. If the expected oxygen output RoC is less than or equal to the oxygen output RoC, the new oxygen output is used to determine an amount of oxygen to add to the bioreactor 150. In some implementations, if the expected oxygen output is greater than the new oxygen output, the determined oxygen output is used to determine an amount of oxygen to add to the bioreactor 150. In some implementations, if the new capacitance measurement is greater than a capacitance threshold, the new oxygen output is used to determine an amount of oxygen to add to the bioreactor 150. The capacitance threshold can be based on a growth phase of the bioreactor 150 and can ensure that the new oxygen output are being used after the growth phase has been completed. In some implementations, the new oxygen output and the new capacitance measurements are used to update the model, as described previously.

Once the type of oxygen output (that is, either the expected oxygen output or the new oxygen output) is determined for use, the computer processors 110 are configured to determine an amount of oxygen to add to the bioreactor based on the determined oxygen output and a desired amount of oxygen output for the bioreactor 150. The desired amount of oxygen output can be based, for example, on requirements for efficient cell culture conditions. The computer processors 110 are configured to operate the valve 140 to cause oxygen to enter the bioreactor 150 through the sparger 130.

Figure 2:
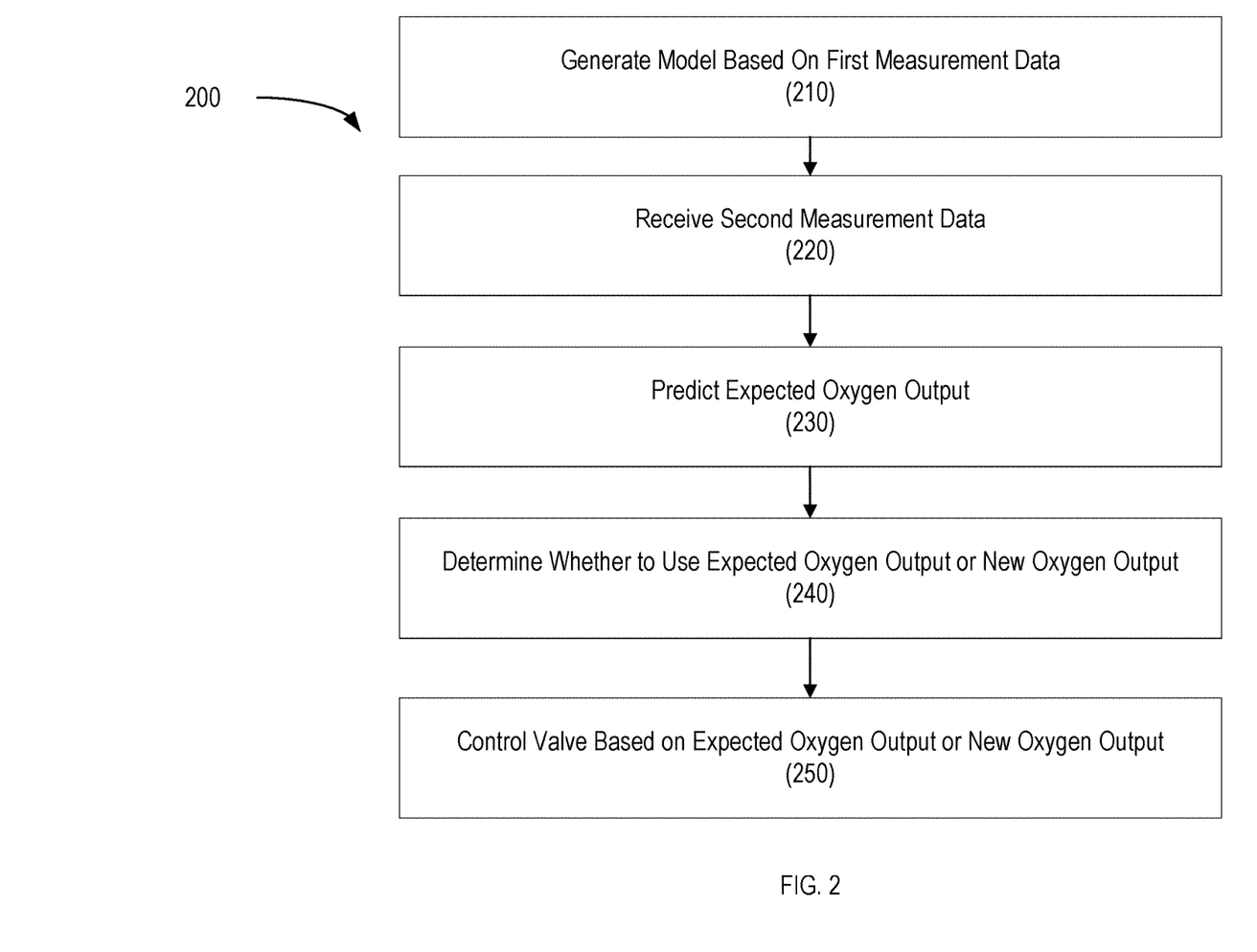
FIG. 2 is a flow diagram illustrating an example method for controlling oxygen levels.

FIG. 2 is a flow diagram illustrating an example method 200 for controlling oxygen levels. In some implementations, method 200 is performed by the computer processors 110 discussed previously with reference to FIG. 1. The method 200 includes generating a model based on first measurement data (block 210); receiving second measurement data (block 220); predicting an expected oxygen output (block 230); determining whether to use the expected oxygen output or a new oxygen output (block 240); and controlling a valve based on the expected oxygen output or the new oxygen output (block 250).

In general, the process 200 can be thought of as performing operations that include sending a DO measurement to a PID to generate an oxygen output; finding a capacitance measurement; establishing a slope between oxygen output and capacitance; generating a rolling average and/or exponential filter of the slope; multiplying the rolling average/exponential filtered slope value by a capacitance to determine an expected oxygen output; determining whether to use expected oxygen output or the new oxygen output; and controlling a valve (actuator) based on expected oxygen output or the new oxygen output value.

At block 210, measurement data is received from one or more sensors (e.g., sensors 120 shown in FIG. 1) representing a set of DO measurements and a set capacitance measurements that were captured over a predetermined time interval. The oxygen output is plotted against corresponding capacitance measurements and an average slope is determined based on the plot.

At block 220, second measurement data is received representing a new DO measurement and a new capacitance measurement.

At block 230, the averaged slope is applied to the new capacitance measurement to determine an expected oxygen output.

At block 240, it is determined whether to use the expected oxygen output or the new oxygen output in determining an amount of oxygen to be added to a bioreactor. In some implementations, the determination is based on a comparison of a DO RoC with a capacitance RoC, as previously described with reference to FIG. 1. In some implementations, the determination is based on a comparison of the expected oxygen output with the new oxygen output, as previously described with reference to FIG. 1.

At block 250, if it is determined to use the expected oxygen output, a control valve is controlled to cause oxygen to enter the bioreactor based on the expected oxygen output. If it is determined to use the new oxygen output, the control valve is controlled to cause oxygen to enter the bioreactor based on the new oxygen output.

Figure 3:
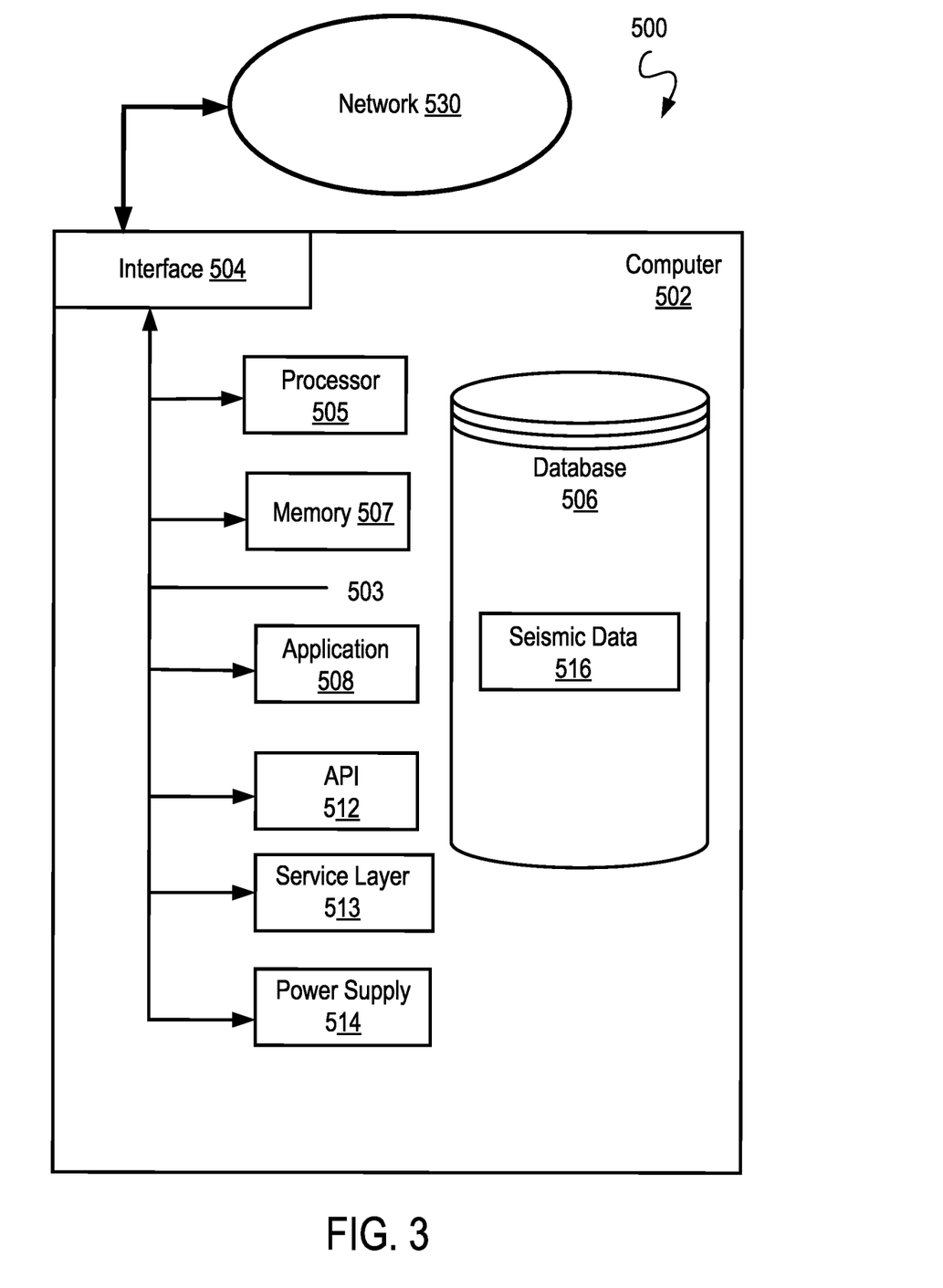
FIG. 3 is a block diagram illustrating an example computer system used to provide computational functionalities associated with described algorithms, methods, functions, processes, flows, and procedures as described in the present disclosure, according to some implementations of the present disclosure.

FIG. 3 is a block diagram of an example computer system 500 used to provide computational functionalities associated with described algorithms, methods, functions, processes, flows, and procedures described in the present disclosure, according to some implementations of the present disclosure. The illustrated computer 502 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 502 can include input devices such as keypads, keyboards, and touch screens that can accept user information. Also, the computer 502 can include output devices that can convey information associated with the operation of the computer 502. The information can include digital data, visual data, audio information, or a combination of information. The information can be presented in a graphical user interface (UI) (or GUI).

The computer 502 can serve in a role as a client, a network component, a server, a database, a persistency, or components of a computer system for performing the subject matter described in the present disclosure. The illustrated computer 502 is communicably coupled with a network 530. In some implementations, one or more components of the computer 502 can be configured to operate within different environments, including cloud-computing-based environments, local environments, global environments, and combinations of environments.

At a high level, the computer 502 is an electronic computing device operable to receive, transmit, process, store, and manage data and information associated with the described subject matter. According to some implementations, the computer 502 can also include, or be communicably coupled with, an application server, an email server, a web server, a caching server, a streaming data server, or a combination of servers.

The computer 502 can receive requests over network 530 from a client application (for example, executing on another computer 502). The computer 502 can respond to the received requests by processing the received requests using software applications. Requests can also be sent to the computer 502 from internal users (for example, from a command console), external (or third) parties, automated applications, entities, individuals, systems, and computers.

Each of the components of the computer 502 can communicate using a system bus 503. In some implementations, any or all of the components of the computer 502, including hardware or software components, can interface with each other or the interface 505 (or a combination of both), over the system bus 503. Interfaces can use an application programming interface (API) 512, a service layer 513, or a combination of the API 512 and service layer 513. The API 512 can include specifications for routines, data structures, and object classes. The API 512 can be either computer-language independent or dependent. The API 512 can refer to a complete interface, a single function, or a set of APIs.

The service layer 513 can provide software services to the computer 502 and other components (whether illustrated or not) that are communicably coupled to the computer 502. The functionality of the computer 502 can be accessible for all service consumers using this service layer. Software services, such as those provided by the service layer 513, can provide reusable, defined functionalities through a defined interface. For example, the interface can be software written in JAVA, C++, or a language providing data in extensible markup language (XML) format. While illustrated as an integrated component of the computer 502, in alternative implementations, the API 512 or the service layer 513 can be stand-alone components in relation to other components of the computer 502 and other components communicably coupled to the computer 502. Moreover, any or all parts of the API 512 or the service layer 513 can be implemented as child or sub-modules of another software module, enterprise application, or hardware module without departing from the scope of the present disclosure.

The computer 502 includes an interface 504. Although illustrated as a single interface 504 in FIG. 3, two or more interfaces 504 can be used according to particular needs, desires, or particular implementations of the computer 502 and the described functionality. The interface 504 can be used by the computer 502 for communicating with other systems that are connected to the network 530 (whether illustrated or not) in a distributed environment. Generally, the interface 504 can include, or be implemented using, logic encoded in software or hardware (or a combination of software and hardware) operable to communicate with the network 530. More specifically, the interface 504 can include software supporting one or more communication protocols associated with communications. As such, the network 530 or the hardware of the interface can be operable to communicate physical signals within and outside of the illustrated computer 502.

The computer 502 includes a processor 505. Although illustrated as a single processor 505 in FIG. 3, two or more processors 505 can be used according to particular needs, desires, or particular implementations of the computer 502 and the described functionality. Generally, the processor 505 can execute instructions and can manipulate data to perform the operations of the computer 502, including operations using algorithms, methods, functions, processes, flows, and procedures as described in the present disclosure.

The computer 502 also includes a database 506 that can hold data (for example, seismic data 516) for the computer 502 and other components connected to the network 530 (whether illustrated or not). For example, database 506 can be an in-memory, conventional, or a database storing data consistent with the present disclosure. In some implementations, database 506 can be a combination of two or more different database types (for example, hybrid in-memory and conventional databases) according to particular needs, desires, or particular implementations of the computer 502 and the described functionality. Although illustrated as a single database 506 in FIG. 3, two or more databases (of the same, different, or combination of types) can be used according to particular needs, desires, or particular implementations of the computer 502 and the described functionality. While database 506 is illustrated as an internal component of the computer 502, in alternative implementations, database 506 can be external to the computer 502.

The computer 502 also includes a memory 507 that can hold data for the computer 502 or a combination of components connected to the network 530 (whether illustrated or not). Memory 507 can store any data consistent with the present disclosure. In some implementations, memory 507 can be a combination of two or more different types of memory (for example, a combination of semiconductor and magnetic storage) according to particular needs, desires, or particular implementations of the computer 502 and the described functionality. Although illustrated as a single memory 507 in FIG. 3, two or more memories 507 (of the same, different, or combination of types) can be used according to particular needs, desires, or particular implementations of the computer 502 and the described functionality. While memory 507 is illustrated as an internal component of the computer 502, in alternative implementations, memory 507 can be external to the computer 502.

The application 508 can be an algorithmic software engine providing functionality according to particular needs, desires, or particular implementations of the computer 502 and the described functionality. For example, application 508 can serve as one or more components, modules, or applications. Further, although illustrated as a single application 508, the application 508 can be implemented as multiple applications 508 on the computer 502. In addition, although illustrated as internal to the computer 502, in alternative implementations, the application 508 can be external to the computer 502.

The computer 502 can also include a power supply 514. The power supply 514 can include a rechargeable or non-rechargeable battery that can be configured to be either user- or non-user-replaceable. In some implementations, the power supply 514 can include power-conversion and management circuits, including recharging, standby, and power management functionalities. In some implementations, the power-supply 514 can include a power plug to allow the computer 502 to be plugged into a wall socket or a power source to, for example, power the computer 502 or recharge a rechargeable battery.

There can be any number of computers 502 associated with, or external to, a computer system containing computer 502, with each computer 502 communicating over network 530. Further, the terms "client," "user," and other appropriate terminology can be used interchangeably, as appropriate, without departing from the scope of the present disclosure. Moreover, the present disclosure contemplates that many users can use one computer 502 and one user can use multiple computers 502.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/-R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of implementations of these systems and methods have been described. However, these systems and methods can include other implementations. For example, although the systems and methods have been described within the context of bioreactors, the systems and methods described can be useful in other contexts. This type of control is similar to hybrid of a model predictive controller with a PID controller. By utilizing the output of the PID controller and determine its relationship or correlation to other measurements within the bioreactor, this can be applied to increase the robustness of control. This type of control scheme can be utilized when there is excessive noise in the input measurement that impacts the output of the PID controller. By augmenting the PID controller with a model, the output of that controller can be modified to be more reliable. This can be implemented by replacing the direct output of the PID with the model expected output, or by imposing constraints on the PID through the expected output from the model. In this instance the control of oxygen with capacitance measurement is demonstrated (Industry first).

What is claimed is:

1. A bioreactor system, comprising:
a bioreactor vessel;
an oxygen supply line;
a control valve that regulates a flow of oxygen through the oxygen supply line into the bioreactor vessel;
a dissolved oxygen (DO) sensor configured to capture measurement data representing DO levels in the bioreactor vessel;
a capacitance sensor configured to capture measurement data representing capacitance levels in the bioreactor vessel;

a computer-readable memory comprising computer-executable instructions; and one or more processors communicatively coupled to the one or more sensors and configured to execute the computer-executable instructions, wherein when the one or more processors are executing the computer-executable instructions, the one or more processors are configured to carry out operations comprising:

receiving first measurement data captured by the DO sensor and the capacitance sensor during a first time interval and representing a first set of DO measurements and a first set of capacitance measurements;

processing the first measurement data to generate data defining a model based on a relationship between the first set of DO measurements and the first set of capacitance measurements;

receiving, from the DO sensor and the capacitance sensor, second measurement data captured by the DO sensor and the capacitance sensor during a second time interval and representing a new DO measurement and a new capacitance measurement;

predicting, using the model and based on the new capacitance measurement, an expected DO measurement;

determining whether to use the expected DO measurement or the new DO measurement for determining an oxygen input amount, comprising:
 determining a DO rate of change based on the new DO measurement and the first set of DO measurements;
 determining a capacitance rate of change based on the new capacitance measurement and the first set of capacitance measurements; and
 determining to use the expected DO measurement when the DO rate of change exceeds the capacitance rate of change by a rate of change threshold; and controlling, when it is determined to use the expected DO measurement, the control valve to cause the determined oxygen input amount to flow through the oxygen supply line into the bioreactor vessel based on the expected DO measurement.

2. The bioreactor system of claim 1, wherein determining whether to use the expected DO measurement or the new DO measurement further comprises:
 comparing the new capacitance measurement with a capacitance threshold; and
 determining to use the new DO measurement when the new capacitance measurement exceeds the capacitance threshold.

3. The bioreactor system of claim 1, wherein determining whether to use the expected DO measurement or the new DO measurement further comprises:
 comparing the expected DO measurement and the new DO measurement; and
 determining to use the expected DO measurement when the expected DO measurement exceeds the new DO measurement.

4. The bioreactor system of claim 1, the operations further comprising:
 receiving third measurement data captured by the DO sensor and the capacitance sensor during a third time interval and representing a third set of DO measurements and a third set of capacitance measurements; and
 updating the model based on the third measurement data.

5. The bioreactor system of claim 1, further comprising:
 updating the model based on the second measurement data.

6. A method for controlling oxygen flow a bioreactor system, wherein the bioreactor system comprises:
 a bioreactor vessel;
 an oxygen supply line;
 a control valve that regulates a flow of oxygen through the oxygen supply line into the bioreactor vessel;
 a dissolved oxygen (DO) sensor configured to capture measurement data representing DO levels in the bioreactor vessel; and
 a capacitance sensor configured to capture measurement data representing capacitance levels in the bioreactor vessel;

the method comprising:

receiving first measurement data captured by the DO sensor and the capacitance sensor during a first time interval and representing a first set of DO measurements and a first set of capacitance measurements;

processing the first measurement data to generate data defining a model based on a relationship between the first set of DO measurements and the first set of capacitance measurements;

receiving, from the DO sensor and the capacitance sensor, second measurement data captured by the DO sensor and the capacitance sensor during a second time interval and representing a new DO measurement and a new capacitance measurement;

predicting, using the model and based on the new capacitance measurement, an expected DO measurement;

determining whether to use the expected DO measurement or the new DO measurement for determining an oxygen input amount, comprising:
 determining a DO rate of change based on the new DO measurement and the first set of DO measurements;
 determining a capacitance rate of change based on the new capacitance measurement and the first set of capacitance measurements; and
 determining to use the expected DO measurement when the DO rate of change exceeds the capacitance rate of change by a rate of change threshold; and controlling, when it is determined to use the expected DO measurement, the control valve to cause the determined oxygen input amount to flow through the oxygen supply line into the bioreactor vessel based on the expected DO measurement.

7. The method of claim 6, wherein determining whether to use the expected DO measurement or the new DO measurement further comprises:
 comparing the new capacitance measurement with a capacitance threshold; and
 determining to use the new DO measurement when the new capacitance measurement exceeds the capacitance threshold.

8. The method of claim 6, wherein determining whether to use the expected DO measurement or the new DO measurement further comprises:
 comparing the expected DO measurement and the new DO measurement; and
 determining to use the expected DO measurement when the expected DO measurement exceeds the new DO measurement.

9. The method of claim 6, further comprising:
 receiving third measurement data captured by the DO sensor and the capacitance sensor during a third time interval and representing a third set of DO measurements and a third set of capacitance measurements; and
 updating the model based on the third measurement data.

10. The method of claim 6, further comprising:
 updating the model based on the second measurement data.

11. A non-transitory computer-readable medium storing instructions that, when executed by one or more processors, cause the one or more processors to perform operations for controlling oxygen flow a bioreactor system, wherein the bioreactor system comprises:
- a bioreactor vessel;
- an oxygen supply line;
- a control valve that regulates a flow of oxygen through the oxygen supply line into the bioreactor vessel;
- a dissolved oxygen (DO) sensor configured to capture measurement data representing DO levels in the bioreactor vessel; and
- a capacitance sensor configured to capture measurement data representing capacitance levels in the bioreactor vessel;
- wherein the operations comprise:
- receiving first measurement data captured by the DO sensor and the capacitance sensor during a first time interval and representing a first set of DO measurements and a first set of capacitance measurements;
- processing the first measurement data to generate data defining a model based on a relationship between the first set of DO measurements and the first set of capacitance measurements;
- receiving, from the DO sensor and the capacitance sensor, second measurement data captured by the DO sensor and the capacitance sensor during a second time interval and representing a new DO measurement and a new capacitance measurement;
- predicting, using the model and based on the new capacitance measurement, an expected DO measurement;
- determining whether to use the expected DO measurement or the new DO measurement for determining an oxygen input amount, comprising:
  - determining a DO rate of change based on the new DO measurement and the first set of DO measurements;
  - determining a capacitance rate of change based on the new capacitance measurement and the first set of capacitance measurements; and
  - determining to use the expected DO measurement when the DO rate of change exceeds the capacitance rate of change by a rate of change threshold; and
- controlling, when it is determined to use the expected DO measurement, the control valve to cause the determined oxygen input amount to flow through the oxygen supply line into the bioreactor vessel based on the expected DO measurement.

12. The non-transitory computer-readable medium of claim 11, wherein determining whether to use the expected DO measurement or the new DO measurement further comprises:
- comparing the new capacitance measurement with a capacitance threshold; and
- determining to use the new DO measurement when the new capacitance measurement exceeds the capacitance threshold.

13. The non-transitory computer-readable medium of claim 11, wherein determining whether to use the expected DO measurement or the new DO measurement further comprises:
- comparing the expected DO measurement and the new DO measurement; and
- determining to use the expected DO measurement when the expected DO measurement exceeds the new DO measurement.

14. The non-transitory computer-readable medium of claim 11, the operations comprising:
- receiving third measurement data captured by the DO sensor and the capacitance sensor during a third time interval and representing a third set of DO measurements and a third set of capacitance measurements; and
- updating the model based on the third measurement data.

15. The non-transitory computer-readable medium of claim 11, further comprising:
- updating the model based on the second measurement data.

16. The bioreactor system of claim 1, wherein the bioreactor vessel comprises organisms submerged in a liquid medium.

17. The bioreactor system of claim 1, wherein the bioreactor vessel comprises organisms attached to a surface of a solid medium.

18. The bioreactor system of claim 1, further comprising an agitator for mixing contents of the bioreactor vessel.

19. The bioreactor system of claim 1, further comprising a sparger coupled to the oxygen supply line.

20. A bioreactor system, comprising:
- a bioreactor vessel;
- an oxygen supply line;
- a control valve that regulates a flow of oxygen through the oxygen supply line into the bioreactor vessel;
- a dissolved oxygen (DO) sensor configured to capture measurement data representing DO levels in the bioreactor vessel;
- a capacitance sensor configured to capture measurement data representing capacitance levels in the bioreactor vessel;
- a computer-readable memory comprising computer-executable instructions; and
- one or more processors communicatively coupled to the one or more sensors and configured to execute the computer-executable instructions, wherein when the one or more processors are executing the computer-executable instructions, the one or more processors are configured to carry out operations comprising:
- receiving first measurement data captured by the DO sensor and the capacitance sensor during a first time interval and representing a first set of DO measurements and a first set of capacitance measurements;
- processing the first measurement data to generate data defining a model based on a relationship between the first set of DO measurements and the first set of capacitance measurements;
- receiving, from the DO sensor and the capacitance sensor, second measurement data captured by the DO sensor and the capacitance sensor during a second time interval and representing a new DO measurement and a new capacitance measurement;
- predicting, using the model and based on the new capacitance measurement, an expected DO measurement;
- determining whether to use the expected DO measurement or the new DO measurement for determining an oxygen input amount, comprising:
  - comparing the new capacitance measurement with a capacitance threshold; and
  - determining to use the new DO measurement when the new capacitance measurement exceeds the capacitance threshold; and
  - determining to use the expected DO measurement when the DO rate of change exceeds the capacitance rate of change by a rate of change threshold; and
- controlling, when it is determined to use the expected DO measurement, the control valve to cause the determined oxygen input amount to flow through the oxygen supply line into the bioreactor vessel based on the expected DO measurement.

21. A bioreactor system, comprising:
a bioreactor vessel;
an oxygen supply line;
a control valve that regulates a flow of oxygen through the oxygen supply line into the bioreactor vessel;
a dissolved oxygen (DO) sensor configured to capture measurement data representing DO levels in the bioreactor vessel;
a capacitance sensor configured to capture measurement data representing capacitance levels in the bioreactor vessel;
a computer-readable memory comprising computer-executable instructions; and
one or more processors communicatively coupled to the one or more sensors and configured to execute the computer-executable instructions, wherein when the one or more processors are executing the computer-executable instructions, the one or more processors are configured to carry out operations comprising:
receiving first measurement data captured by the DO sensor and the capacitance sensor during a first time interval and representing a first set of DO measurements and a first set of capacitance measurements;
processing the first measurement data to generate data defining a model based on a relationship between the first set of DO measurements and the first set of capacitance measurements;
receiving, from the DO sensor and the capacitance sensor, second measurement data captured by the DO sensor and the capacitance sensor during a second time interval and representing a new DO measurement and a new capacitance measurement;
predicting, using the model and based on the new capacitance measurement, an expected DO measurement;
determining whether to use the expected DO measurement or the new DO measurement for determining an oxygen input amount, comprising:
  comparing the expected DO measurement and the new DO measurement; and
  determining to use the expected DO measurement when the expected DO measurement exceeds the new DO measurement; and
  determining to use the expected DO measurement when the DO rate of change exceeds the capacitance rate of change by a rate of change threshold; and
controlling, when it is determined to use the expected DO measurement, the control valve to cause the determined oxygen input amount to flow through the oxygen supply line into the bioreactor vessel based on the expected DO measurement.

* * * * *